(12) United States Patent
Nomoto et al.

(10) Patent No.: US 7,119,908 B2
(45) Date of Patent: *Oct. 10, 2006

(54) METHOD AND APPARATUS FOR MEASURING THICKNESS OF THIN FILM AND DEVICE MANUFACTURING METHOD USING SAME

(75) Inventors: Mineo Nomoto, Yokohama (JP); Takenori Hirose, Machida (JP); Keiya Saito, Hiratsuka (JP)

(73) Assignee: Hitachi, Ltd., Tokyo (JP)

( * ) Notice: Subject to any disclaimer, the term of this patent is extended or adjusted under 35 U.S.C. 154(b) by 536 days.

This patent is subject to a terminal disclaimer.

(21) Appl. No.: 10/082,430

(22) Filed: Feb. 22, 2002

(65) Prior Publication Data

US 2005/0117164 A1 Jun. 2, 2005

(30) Foreign Application Priority Data

Jul. 27, 2001 (JP) .............................. 2001-226984

(51) Int. Cl.
*G01B 11/02* (2006.01)
(52) U.S. Cl. ...................................... 356/504
(58) Field of Classification Search ................ 356/497, 356/503, 504; 438/14, 16
See application file for complete search history.

(56) References Cited

U.S. PATENT DOCUMENTS

| 5,087,121 | A | | 2/1992 | Kakuchi et al. |
| 6,004,187 | A | * | 12/1999 | Nyui et al. ..................... 451/5 |
| 6,159,073 | A | * | 12/2000 | Wiswesser et al. ............ 451/6 |
| 6,271,047 | B1 | | 8/2001 | Ushio et al. |
| 6,425,801 | B1 | | 7/2002 | Takeishi et al. |
| 6,503,361 | B1 | | 1/2003 | Nyui et al. |
| 6,551,172 | B1 | | 4/2003 | Nyui et al. |
| 6,670,200 | B1 | | 12/2003 | Ushio et al. |
| 6,963,407 | B1 | * | 11/2005 | Abe et al. ................... 356/503 |
| 2002/0197871 | A1 | | 12/2002 | Hirose et al. |
| 2003/0022400 | A1 | * | 1/2003 | Nomoto et al. ............... 438/14 |

FOREIGN PATENT DOCUMENTS

| JP | 06-252113 | 9/1994 |
| JP | 09-007985 | 1/1997 |
| JP | 10-083977 | 3/1998 |
| JP | 10-294297 | 11/1998 |
| JP | 2000-077371 | 3/2000 |
| JP | 2000-310512 | 11/2000 |

* cited by examiner

*Primary Examiner*—Gregory J. Toatley, Jr.
*Assistant Examiner*—Michael A. Lyons
(74) *Attorney, Agent, or Firm*—Townsend and Townsend and Crew LLP

(57) ABSTRACT

A manufacturing method and manufacturing device for high-precision thin film devices is disclosed, whereby the film thickness and film thickness distribution of a transparent film is measured to a high degree of accuracy during a CMP process without being affected by the film thickness distribution between LSI regions or within the semiconductor wafer surface generated by CMP processing. Film thickness is measured by specifying relatively level measurement regions, according to a characteristic quantity of the spectral waveform of the reflected light from the transparent film, such as the reflection intensity, frequency spectrum intensity, or the like, thereby permitting highly accurate control of film thickness. The leveling process in CMP processing can be optimized on the basis of the film thickness distribution. The film deposition conditions in the film deposition stage and the etching conditions in the etching stage can also be optimized. Accordingly, a high-precision semiconductor device can be manufactured.

11 Claims, 15 Drawing Sheets

(A) WIRING CIRCUIT
PATTERN SECTION (B) PERIPHERAL CIRCUIT
PATTERN SECTION (a) WIRING CIRCUIT SECTION (b) MEMORY CIRCUIT SECTION (c) PERIPHERAL CIRCUIT SECTION (a)                    (b)

(c)

(a)　　　　　　　　　(b)

METHOD AND APPARATUS FOR MEASURING THICKNESS OF THIN FILM AND DEVICE MANUFACTURING METHOD USING SAME

The present invention relates to a method for manufacturing semiconductor devices while measuring the thickness and thickness distribution of transparent films and for controlling the film thickness. For example, the invention relates to a method for measuring the uppermost film thickness of a wafer in a surface leveling process after film deposition, the leveling process itself being controlled by measuring the film thickness. Examples of such transparent films include resist films, insulating films, and the like, in manufacturing stages of thin film devices, such as DVD, TFT (Thin Film Transistor) and LSI (Large Scale Integration) reticles, and the like.

Semiconductor devices are manufactured by forming devices and wiring patterns onto and into a silicon wafer by means of film deposition, exposure and etching processes. In recent years, to achieve higher precision and higher density in such devices, greater film thinness and increased layering have resulted in an increase in the number of indentations in the wafer surface. Such indentations impede the light exposure process, which is essential in forming wiring, and the like. Accordingly, the wafer surface is leveled, for example, by a chemical mechanical polishing (CMP) process. A CMP technique, in which the wafer surface is leveled by chemical and physical polishing, is used for this process. CMP is a now well known technique.

A principal problem involved with CMP processing is controlling film thickness. In particular, it is necessary to reduce variation in the high-precision evenness and film thickness of the wafers by incorporating an in-situ measuring system into the CMP system to measure the film thickness during the CMP process. This enables stopping the process when the wafer has been processed to a prescribed film thickness. Consequently, a variety of methods have been proposed as in-situ measurement techniques.

Japanese Patent Laid-open No. (Hei)6-252113 and Japanese Patent Laid-open No. (Hei)9-7985 disclose in-situ measuring systems capable of measuring the film thickness over the actual device pattern (at the fine circuit pattern constituting the actual product). In Japanese Patent Laid-open No. (Hei)6-252113, the spectrum of the interference pattern produced on the film by white light is analyzed with respect to frequency, and the absolute value of the thin film is calculated by observing the relationship between the frequency component related to the spectral waveform and the film thickness. In Japanese Patent Laid-open No. (Hei) 10-83977, the intensity of the interference pattern produced on the transparent film by a laser (single-wavelength source) changes with respect to the processing time. The change in intensity is detected and the film thickness is calculated from the frequency component related to that waveform.

Japanese Patent Laid-open No. (Hei)10-294297 and Japanese Patent Laid-open No. 2000-77371 disclose techniques for performing in-situ measurement by specifying measurement positions. In Japanese Patent Laid-open No. (Hei) 10-294297, the measurement positions are specified by extracting the characteristics of the image of the circuit pattern or by forming a diffraction pattern in the scribe area of the pattern. In Japanese Patent Laid-open No. 2000-77371, the maxima and minima of the spectral waveform are observed, and measurement points for measuring the film thickness during processing are specified by comparison of these parameters with previously measured maxima and minima of spectral waveforms.

Generally, there have been problems in controlling film thickness with high accuracy by using the CMP processing time, because the amount of polishing (polishing rate) per unit time varies, and the polishing rate also differs according to the ratio of the wafer plane occupied by the pattern formed thereon (herein, "pattern area ratio"). FIG. 17 shows the film thickness distribution measurement results for a semiconductor device measured using the technique disclosed in Japanese Patent Laid-open No. 2000-310512. FIG. 17 illustrates film thickness distribution measurement results 160 for a transparent film (insulating film between layers) having an area of approximately 20 mm on a wafer that has been CMP processed. It also shows the film thickness distribution in the wiring pattern sections 161, 162, peripheral circuit section 163, and the border sections 164, 165 between the peripheral circuit section and the wiring pattern sections. As these film thickness distribution measurement results 160 show, a film thickness change of several hundreds of nanometers occurs in a region of approximately 2 mm at border sections 164, 165 between the peripheral circuit section and the wiring pattern sections. On the other hand, the wiring pattern sections 161, 162 and the peripheral circuit section 163 have a comparatively even film thickness over regions of several mm.

This film thickness distribution is produced by the pattern area ratio and the processing conditions, such as the type of polishing pad in the processing device, the type of polishing fluid (slurry), and the like, and it may vary with the products used or with each wafer, due to variations in the type of semiconductor circuit pattern and in the processing conditions (state of wear of the polishing pad, density of slurry, and the like). As described above, in in-situ measurement during the CMP process, a problem arises: depending on the observed field being measured, the measurement accuracy declines as regions having great variation in film thickness for measurement. Furthermore, although Japanese Patent Laid-open No. (Hei)10-294297 and Japanese Patent Laid-open No. 2000-77371 disclose methods for specifying measurement points, even in those disclosures, no particular attention is given to the measurement fields, which are specified over a relatively large region (diameter of approximately 2 mm). Hence there is a risk that measurement accuracy will decline when the film thickness is measured in a state such as that illustrated in FIG. 17.

The spectral waveform provides waveform data that includes information from a broad area of varying film thickness and underneath wiring; hence it is difficult to specify the desired measurement points. Therefore, it is not possible to reduce fluctuation in high-precision evenness and film thickness characteristics by terminating the CMP processing at the moment that the wafer has been processed to a prescribed film thickness. This makes it difficult to control film thickness to a high degree of accuracy, and leads to a decline in semiconductor device yield.

Slurry has been conventionally used as a polishing fluid in CMP processing. In Japanese Patent Laid-open No. (Hei) 10-83977, in-situ measurement is conducted by forming a transparent window in the polishing band and extracting the spectral waveform from the wafer surface in the slurry. Because the slurry is a polishing fluid containing particles of silica, potassium hydroxide, and the like, it is optically semitransparent, and has poor light transmission characteristics. Furthermore, the spectral reflectivity of the wafer surface is also reduced markedly by the occurrence of glass-type indentations in the transparent window due to the action of the particles contained in the polishing fluid. Consequently, the spectrum cannot be measured in a stable fashion, making it difficult to achieve high-precision control of the film thickness by terminating CMP processing at the moment that the wafer has been processing to a prescribed film thickness.

BRIEF SUMMARY OF THE INVENTION

This invention provides a method and device whereby the thickness of a transparent film can be measured to a high degree of accuracy during a CMP process without being affected by the film thickness distribution in the LSI region arising in the CMP process. The present invention further provides a manufacturing method and manufacturing device for thin film devices using the aforementioned method and device.

Moreover, the present invention provides a method and device whereby the thickness of a transparent film can be measured to a high degree of accuracy by specifying desired measurement positions and a desired measurement field, during a CMP process, without being affected by the film thickness distribution in the LSI region or the film thickness distribution in the wafer surface arising in the CMP process. The film thickness measurement results are used in processing conditions for manufacturing processes that follow CMP processing (etching, film deposition, and the like). The invention further provides a manufacturing method and manufacturing device for thin film devices.

Furthermore, the present invention provides a method and device whereby the thickness of a transparent film can be measured to a high degree of accuracy by extracting a spectral waveform having a high S/N ratio, during a CMP process, without being affected by reduction of the spectral transmission characteristics caused by the slurry during CMP processing.

In addition, the present invention provides a method and device whereby the thickness of a transparent film can be measured to an accuracy of several tens of nm or less over the actual device pattern, for example, during a CMP process, without being affected by the film thickness distribution. In other words, the present invention provides a method and device capable of high-precision control of film thickness, and a method and device for achieving improved process throughput, wherein the film thickness of the uppermost surface over the actual device pattern after CMP processing is measured by using a measurement technique, for example, similar to that disclosed in the Japanese Patent Laid-open No. 2000-310512. The film thickness distribution in the LSI region is extracted and a measurement field and measurement positions are determined on the basis of this film thickness distribution. The spectral waveform is then extracted from the desired measurement field and measurement positions of the device pattern during CMP processing.

In the present invention, the field and measurement positions for measuring the thickness of the transparent film during CMP processing are determined on the basis of the measurement results for film thickness distribution in the LSI region of the actual device pattern following CMP processing. The technique for measuring the actual device pattern is such that the film thickness distribution of the device pattern is measured using a method (herein referred to as an actual-pattern-film-thickness measuring method) such as that disclosed in Japanese Patent Laid-open No. 2000-310512. A desired measurement field is determined on the basis of these measurement results.

From the example results in FIG. 17, taking the measurement field preferably as approximately 50–100 µm diameter, a field of view is adapted which ensures high measurement precision, even if the film thickness changes suddenly (a change of several hundreds of nm in thickness in approximately 1 mm). If the film thickness distribution is flat in the LSI region, then a larger measurement field of several mm can be adopted.

Preferably, the measurement positions are selected such that the film thickness in relatively flat regions 161, 162, as indicated in FIG. 17, can be measured to a high degree of accuracy. Regions 161 and 162 are wiring circuit pattern sections. Since they are stable and have a wiring pattern density below the transparent film of approximately several tens of percent, these regions have good evenness during CMP processing. In a semiconductor manufacturing process, there are wiring regions where interlayer connections are made by forming contact holes, or the like. Preferably, the film thickness of these wiring circuit regions is controlled to determine etching conditions, or other process parameters. The measurement position determining method, according to a preferred embodiment of the present invention, is carried out by using one or more of the following techniques:

(1) extracting the intensity difference in the spectrum of the reflected light;

(2) extracting the frequency spectrum intensity in the spectrum of the reflected light; and (3) comparing spectral waveforms measured by an actual-pattern-film-thickness measurement method.

According an embodiment of the present invention, it is possible to control the film thickness in particular positions, by selecting measurement positions from a characteristic quantity of the spectral wavelength from locations such as the LSI peripheral circuit section, scribe area, or the like, and not only from the wiring regions.

The foregoing description relates to determining the measurement field and measurement positions in the LSI region (chip region) formed on a semiconductor wafer. It is also possible to perform film thickness control in the wafer surface. CMP processing is implemented while the wafer rotates and slides in the CMP apparatus.

In the present invention, the orientation flat position and notch position in the wafer are held in an approximately registered fashion in the wafer holder. The measurement position of the in-situ film thickness measurement system during CMP is judged to be either in the central portion or the peripheral portion of the wafer, on the basis of the orientation flat position and the notch position. The measurement is made, and the result is output.

Moreover, in the present invention, to measure the spectral waveform of the wafer surface at a high S/N ratio through optically transparent slurry, the slurry can be diluted by supplying optically transparent fluid, such as pure water, or the like, in the vicinity of the spectral waveform being measured. By using a material having a refraction index proximate to that of the slurry as the material of the transparent window used for spectral waveform measurement, the increase in reflectivity (increase in spectral transmissivity) due to the difference in the refraction index at the border between the slurry and the transparent window can be reduced. Therefore, the precision of the film thickness control can be improved by extracting a spectral waveform of high S/N ratio even during CMP processing.

These and other objects, features and advantages of the invention will be apparent from the following detailed description of the preferred embodiments of the invention, as illustrated in the accompanying drawings.

DESCRIPTION OF THE PREFERRED EMBODIMENTS

An embodiment of the present invention is described below in which a method for measuring the thickness of transparent film formed on a wafer surface to an accuracy of several tens of nm or less over the actual device pattern, is applied with respect to a CMP processing stage in the manufacture of a semiconductor.

Figure 1:
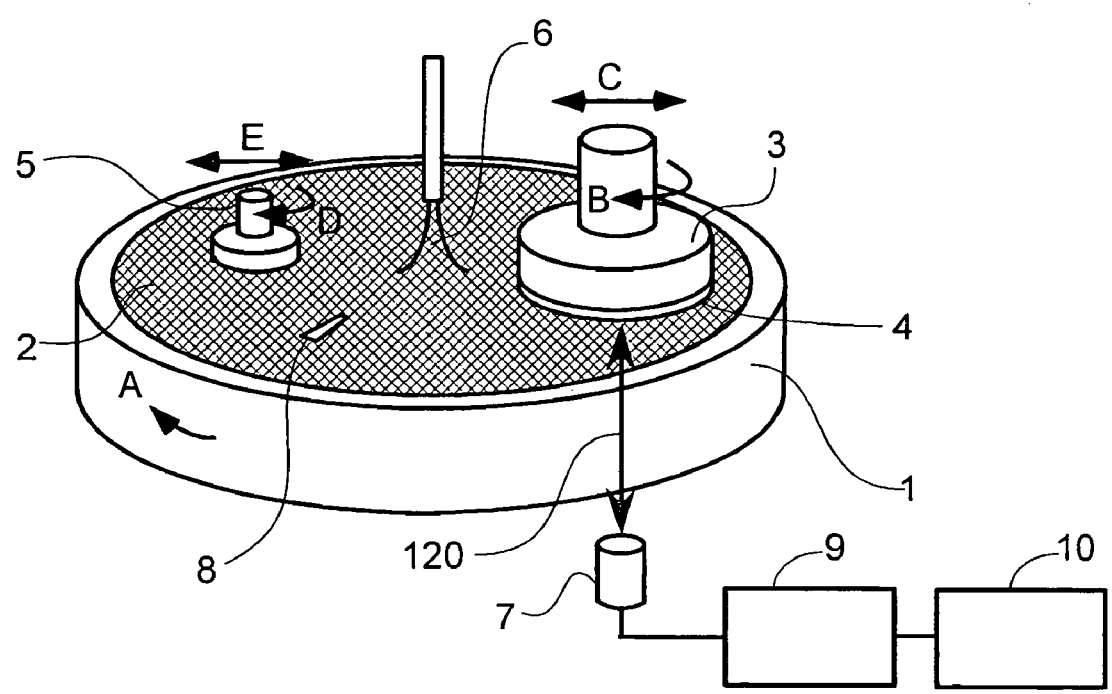
FIG. 1 is a perspective view showing the general composition of a CMP polishing device provided with film thickness measuring means according to an embodiment of the present invention.

FIG. 1 shows an embodiment wherein the film thickness control method according to the present invention is applied to a CMP device. The CMP device comprises a polishing pad 2 formed on a polishing base 1, the wafer 4 to be processed being held in a holder 3. The pad is periodically dressed by a dresser 5, disposed above polishing pad 2, which dresses the pad surface in a manner such that a uniform processing rate is maintained. A structure is provided for supplying a liquid slurry 6 containing polishing granules onto the polishing pad.

To measure the film thickness during CMP processing, a configuration is used whereby a measurement optics system 7 is able to measure the spectral waveform of the wafer surface from below the polishing base 1, by means of a measurement window 8 provided in polishing pad 2. A film thickness measurement controller 9 calculates the film thickness from the measured spectral waveform. This film thickness measurement controller 9 is connected to an actual-pattern-film-thickness measuring device 10 and obtains information from measuring device 10. Measuring device 10 is a measuring system such as that disclosed in Japanese Patent Laid-open No. 2000-310512, whereby the film thickness distribution for processed wafers of a type similar to wafer 4 has been previously measured. Based on these film thickness distribution measurement results, a measurement conditions controller 11 (shown in FIG. 2) selects the measurement fields to be used by measurement optics system 7. The spectral waveforms corresponding to the film thickness at each respective measurement position are detected and input to film thickness measurement controller 9.

The whole surface of the wafer 4 is polished by rotating the polishing base 1 in the direction of arrow A, while holder 3 is made to rotate as indicated by arrow B, and is made to slide as indicated by arrow C. During this process, dresser 5 periodically dresses pad 2 by rotating as indicated by arrow D and by sliding as indicated by arrow E. In the aforementioned configuration, (shown in greater detail in FIG. 2), as polishing base 1 rotates, a window glass 81 incorporated into measurement window 8 passes through measurement light path 120 of measurement optics system 7 once for each revolution of polishing base 1. The spectral waveform of wafer 4 is detected by measurement optics system 7, and the detected spectral waveform is input to the film thickness measurement controller 9, which calculates the film thickness at prescribed measurement positions.

Figure 2:
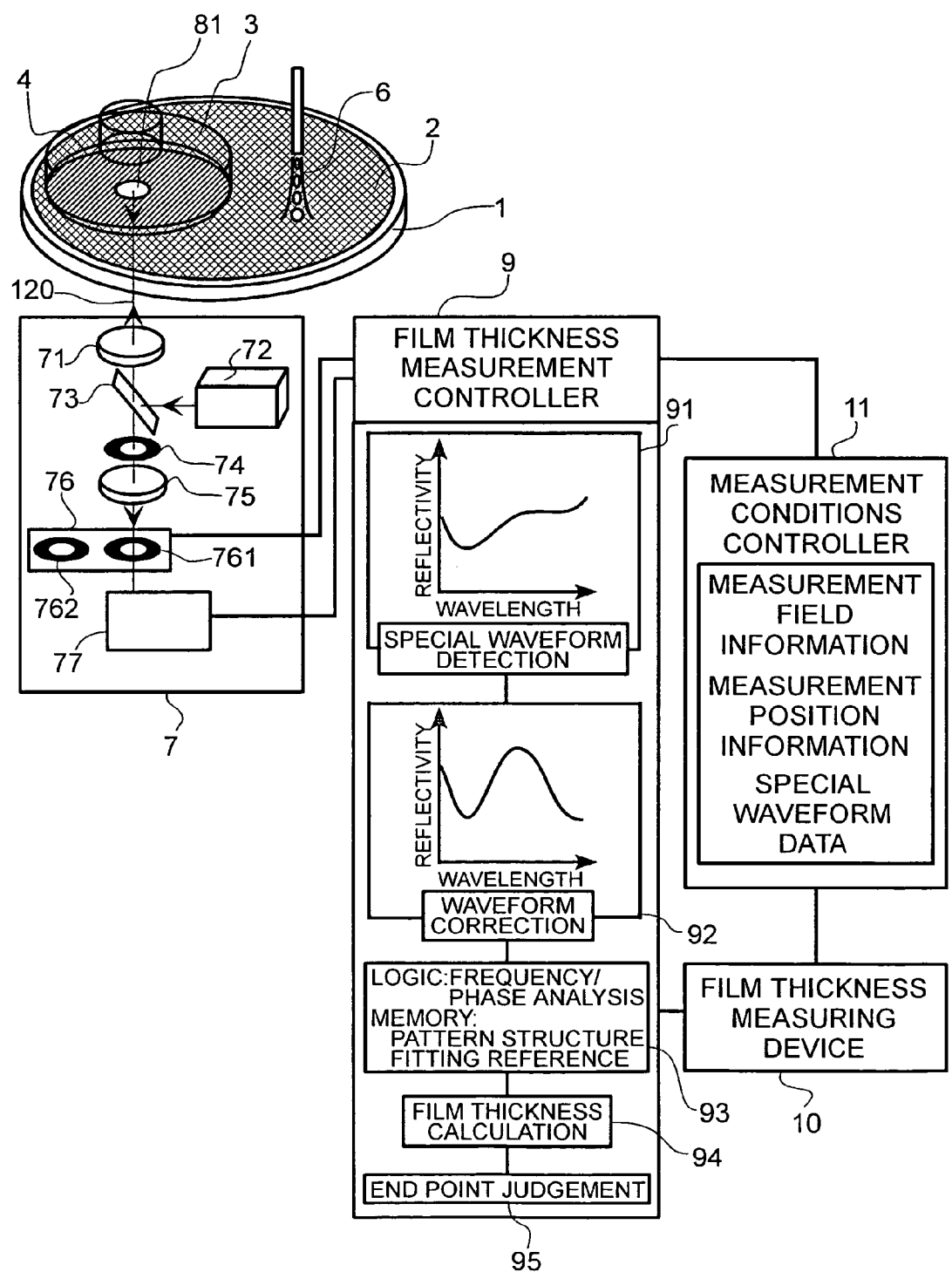
FIG. 2 is a perspective view showing a specific example of a CMP polishing device composition provided with film thickness measuring means according to the present invention.

FIG. 2 shows detailed examples of the measurement optics system 7 and film thickness measurement controller 9 in FIG. 1. Measurement optics system 7 comprises a detecting lens 71, an illuminating light source 72, a half mirror 73, a spatial filter 74, a focusing lens 75, a field of view aperture unit 76, a first field aperture 761, a second field aperture 762, and a beam splitter 77. In this system, white illumination light (wavelength 300 nm–800 nm approx.) is irradiated from the illuminating light source, through half-mirror 73, detecting lens 71 and window glass 81, onto the wafer 4 being processed. The light reflected back by wafer 4 passes through spatial filer 74, focusing lens 75, and field aperture 761, to beam splitter 77, where it is split. The split wavelength signal is measured by film thickness measurement controller 9, which performs wavelength correction processing 92 to remove the effects of wavelength distortion due to the slurry (described below) from resulting spectral waveform 91. A film thickness calculation 94 for the film over the device pattern during processing is made from the corrected spectral waveform by means of a frequency/phase analysis measurement method or a pattern-structure-fitting measurement method, as disclosed in Japanese Patent Laid-open No. 2000-310512. Processing is terminated when the wafer has been processed to a prescribed film thickness. Furthermore, measurement conditions controller 11 inputs measurement field information and spectral waveform data based on the film thickness distribution supplied by actual-pattern-film-thickness measuring device 10 to film thickness controller 9.

Film thickness controller 9 determines whether or not the detected spectral waveform 91 is applicable as film thickness measurement data, selects a spectral waveform required for measurement, and uses that waveform to calculate the film thickness. The measurement field is set as a parameter prior to the start of film thickness measurement, and the prescribed measurement field is set by switching aperture unit 76 of measurement optics system 7 to determine the field aperture diameter. Spatial filter 74 of system 7 is able to remove diffraction harmonics caused by the light scattered at the edges of the wiring patterns and the N.A of the detecting lens. Thus, wavelength distortion, such as significant distortion of the spectral waveform due to diffracted light, is reduced, thereby improving the S/N characteristics of the spectral waveform.

Figure 3:
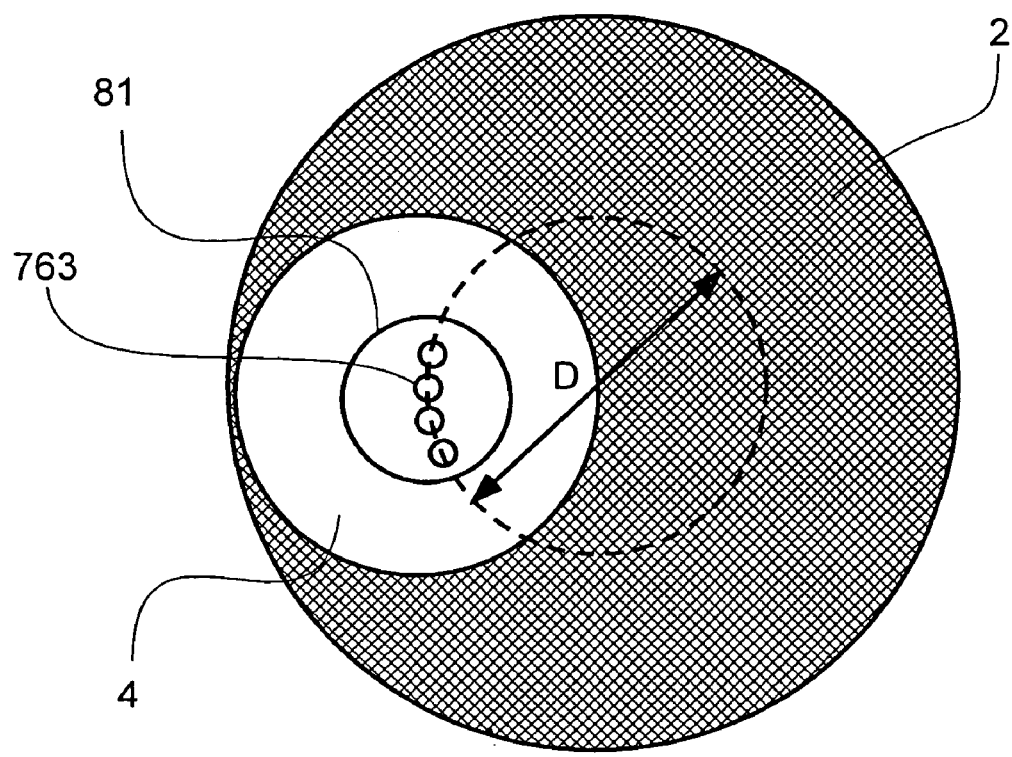
FIG. 3 is a plan view of a polishing pad placed on a wafer, to illustrate a measurement field according to the present invention.

FIG. 3 is a diagram for describing a measurement field in the present embodiment. This conceptual diagram shows an example wherein the window glass 81 as shown in FIG. 3 is 10–50 mm in size, and the detection field of the measurement field of view 763 is 50–100 μm in diameter, the magnification factor of the optics system having been taken into account when the field-of-view size for measuring the spectral waveform was determined. In one revolution of polishing base 1, the spectral waveform data for a plurality of locations on wafer 4 is obtained via window glass 81. In the embodiment in FIG. 3, a state is depicted where spectral data is detected four times, but the higher the number of measurement points, the greater the ability to perform high-precision film thickness evaluation. In practice, the number of measurement samples is determined according to the number of revolutions of polishing base 1 of the CMP device, the size of the measurement window, the sampling rate of the spectral analyzer, the quantity of light produced by the illumination system, the amount of light reflected by the wafer, and the like. In the example shown in FIG. 3, taking the diameter of the polishing base as Dφ=250 mm, the number of revolutions as 100 rpm, and the sampling rate of spectral analyzer as 1 mm/s, an area of φ=50 μm×0.4 mm width is measured. If window glass 81 has a diameter of 10 mm, then 10 measurements can be made. In other words, the required spectral waveform is selected from the spectral data for 10 locations on wafer 4 during one revolution of polishing base 1, and these waveforms are input to film thickness controller 9, which calculates the corresponding film thicknesses.

Figure 4:
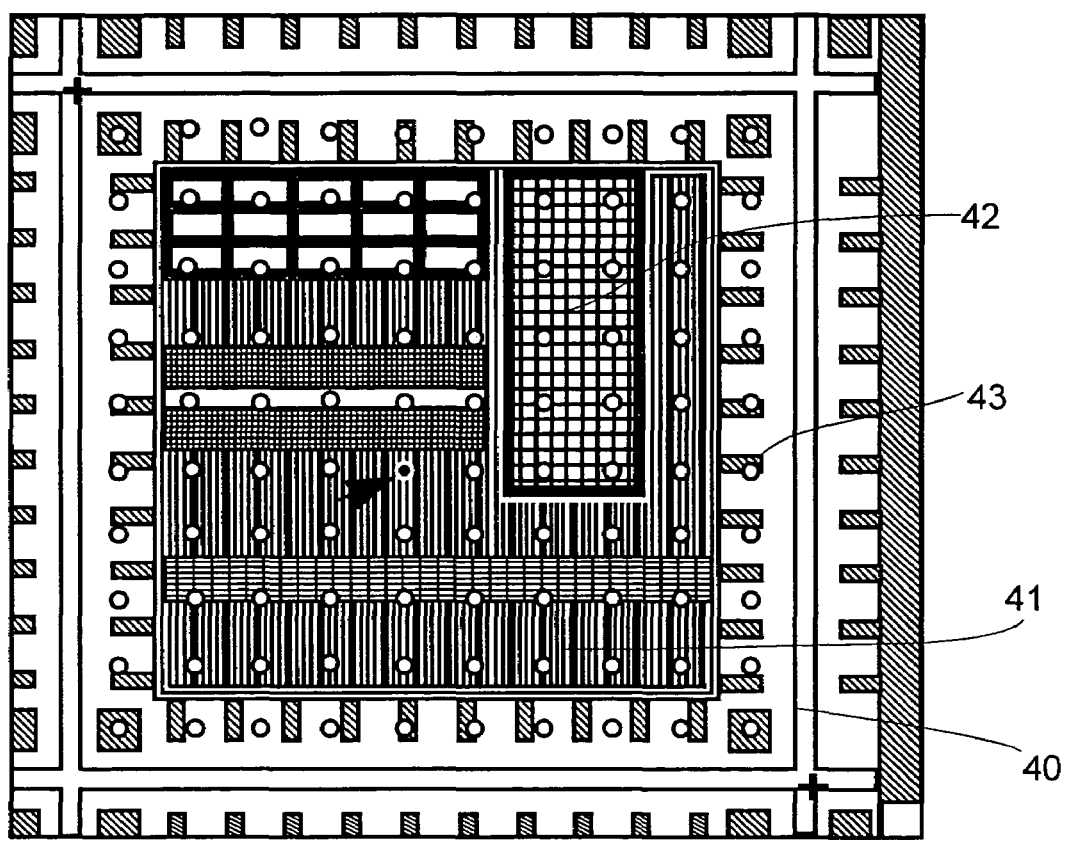
FIG. 4 is a plan view of a semiconductor LSI circuit pattern.

Next, the present invention is described in concrete terms by reference to FIGS. 4–7. FIG. 4 is an example of an LSI circuit 40 (one chip). A circuit wiring pattern section 41 is formed in the central region of the LSI circuit; a portion of the circuit is formed with a memory circuit section 42 having a regulation wiring pattern, and a peripheral circuit pattern section 43 is formed about the periphery of section 41.

Figure 5:
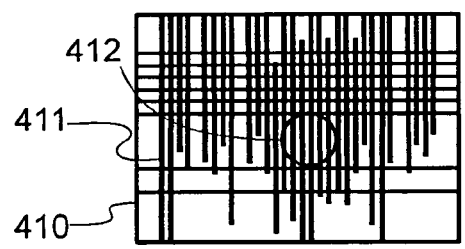
FIG. 5 is a plan view of a semiconductor LSI circuit pattern showing one detailed example of a semiconductor LSI circuit pattern and a measurement field.
Figure 5:
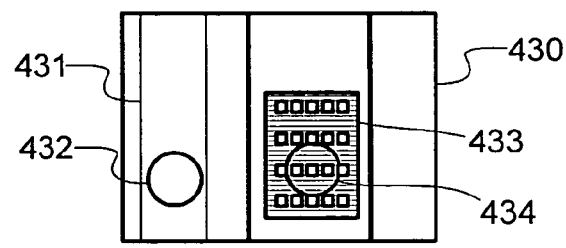

FIG. 5 is a partial enlarged view of FIG. 4, illustrating the relationships between the respective wiring sections and the field of view in a case where a measurement field of 100 μm diameter is used. FIG. 5(*a*) shows circuit wiring pattern section 410, and FIG. 5(*b*) shows a peripheral circuit pattern section 430.

In the most recent LSIs, the wiring pattern 411 is formed to a width of between a tenth and several microns. Taking the measurement field 412 as having a 100 μm diameter, the surface ratio of measurement field 412 that is occupied by the pattern will be several ten percents. On the other hand, the peripheral circuit patterns 431, 433, are formed to a width of several tens of microns to several hundreds of microns. Therefore taking the measurement field 432 as having a 100 μm diameter, the surface ratio occupied by the pattern in measurement field 432 will be 50%–100%.

Figure 6:
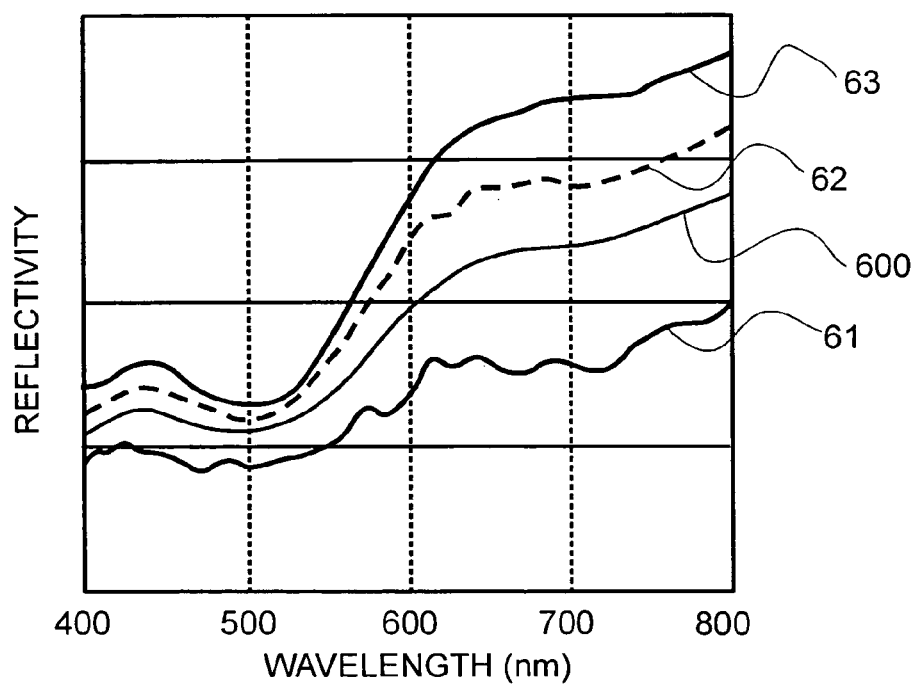
FIG. 6 is a graph showing one example of spectral reflection characteristics from a circuit pattern according to the present invention.

FIG. 6 shows spectral reflection characteristics for the measurement field regions illustrated in FIG. 5. The spectral waveform 61 is measured using measurement field 412 in FIG. 5; spectral waveform 62, using measurement field 434 in FIG. 5; and spectral waveform 63, using measurement field 432 in FIG. 5. These measurements include the slurry; therefore a distorted waveform results. The trend of the waveform distortion is represented by curve 600. Calculation and use of a corrected waveform is discussed later in conjunction with FIG. 11.

Figure 7:
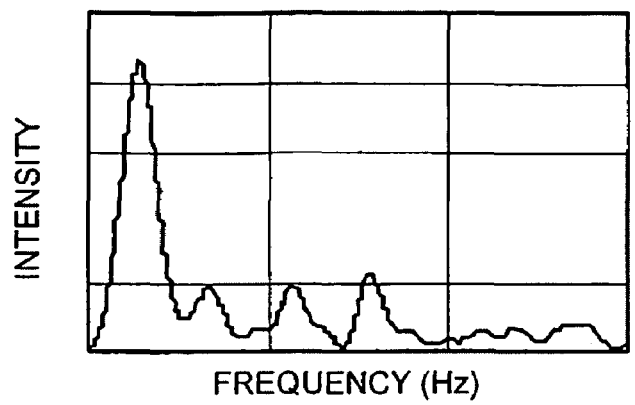
FIGS. 7a–7c are graphs, each showing one example of spectral intensity characteristics from a circuit pattern according to the present invention.
Figure 7:
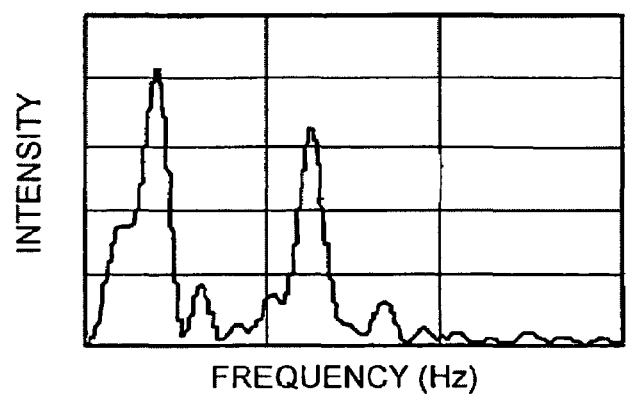
Figure 7:
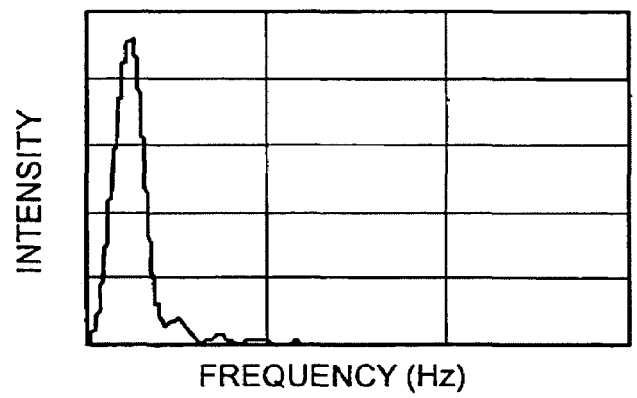

FIG. 7 shows the frequency spectral characteristics for the measurement field regions illustrated in FIG. 5. Specifically, it can be seen that the spectral reflection characteristics vary according to the area ratio of the lower pattern section in the measurement field. If the area ratio occupied by the lower pattern in the measurement field is high, then the spectral reflectivity is high, whereas if this surface area is low, then the reflectivity is low. This tendency is particularly marked in the longer wavelength region. FIG. 7 also shows the frequency spectral characteristics for the measurement field regions illustrated in FIG. 4. FIG. 7(*a*) shows frequency spectrum characteristics for a wiring section. FIG. 7(*b*) shows similar characteristics for a memory section, while FIG. 7(*c*) shows similar characteristics for a peripheral circuit section. It can be seen that, since the spectral characteristics vary according to the form of the wiring pattern occupying the measurement field, the measurement positions can be specified from the frequency spectrum of the spectral waveform.

Since the characteristics of the spectral waveforms shown in FIGS. 6 and 7 are reproducible for respective wiring sections, it is possible to specify measurement positions by comparing and evaluating similar spectral waveforms and reflectivity, or frequency spectrum characteristics, or the like, on the basis of the spectral waveform data from actual-pattern-film-thickness measuring device 10 illustrated in FIG. 2.

Figure 8:
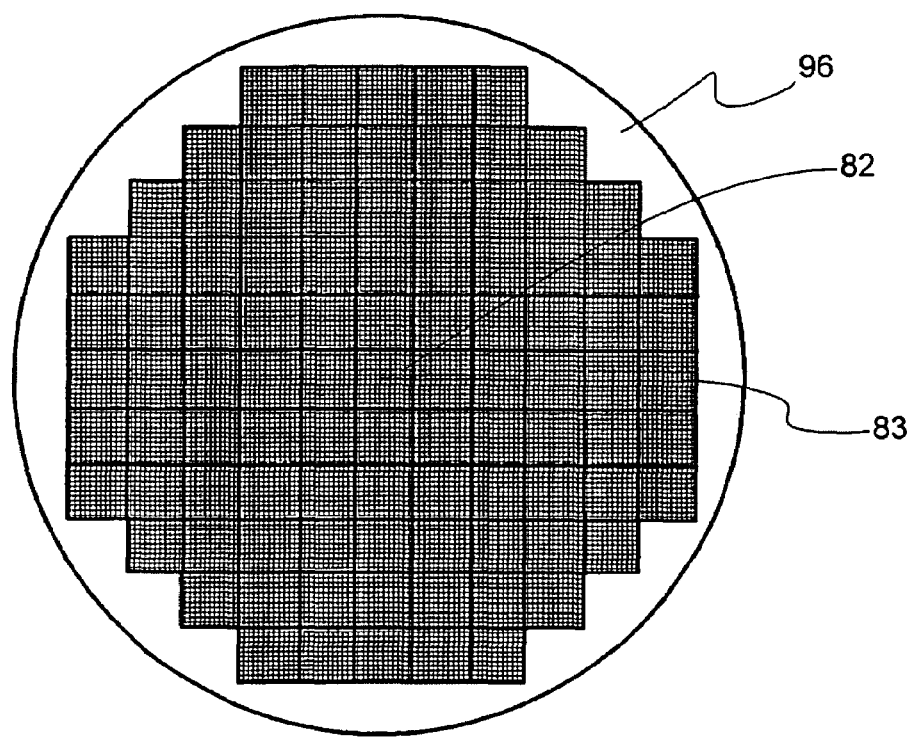
FIG. 8 is a plan view of a semiconductor LSI wafer.
Figure 9:
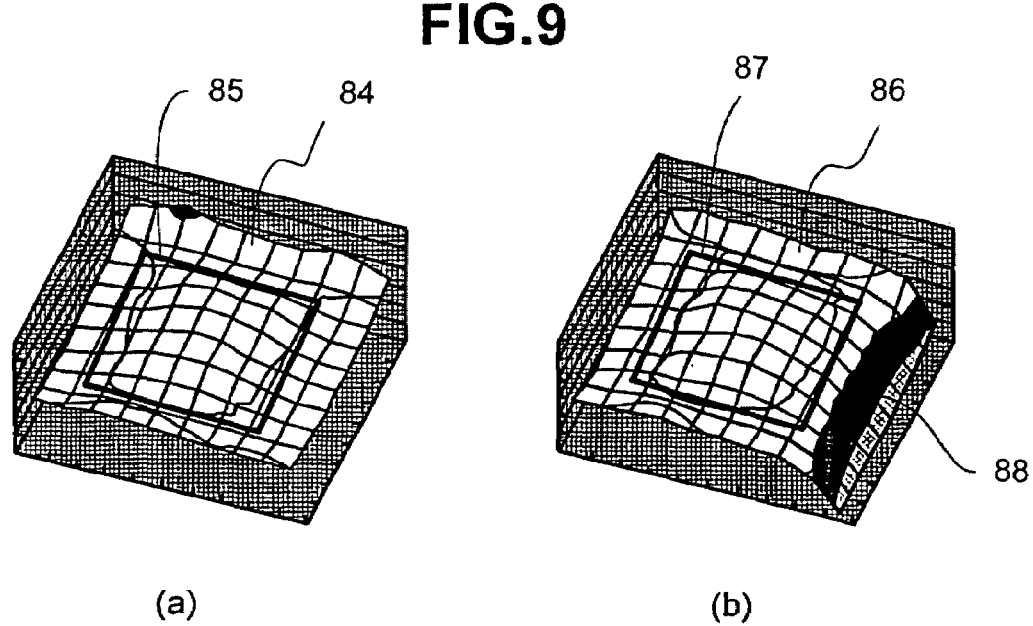
FIGS. 9a–9b are perspective views, each showing one example of the thickness distribution of a transparent film in a semiconductor LSI.

FIG. 8 is a schematic diagram of a semiconductor wafer. FIG. 9 shows an example of film-thickness-distribution measurement results obtained by actual-pattern-film-thickness measuring device 10 measuring the film thickness in a central portion 82 and a peripheral portion 83 of the chip in FIG. 8. The measurement results for the center chip in FIG. 8 indicate that the film in the center region is slightly thicker and that in the peripheral region is slightly thinner. In FIG. 9(*a*), the whole chip is flat compared to FIG. 9(*b*). In FIG. 9(*b*), the outermost periphery 88 of the chip has a notably thinner film thickness. On the outermost border 96 of the chip, as shown in FIG. 8, no pattern is formed, and it is thought that because the CMP processing rate will be great here, the film will be thinner.

Figure 17:
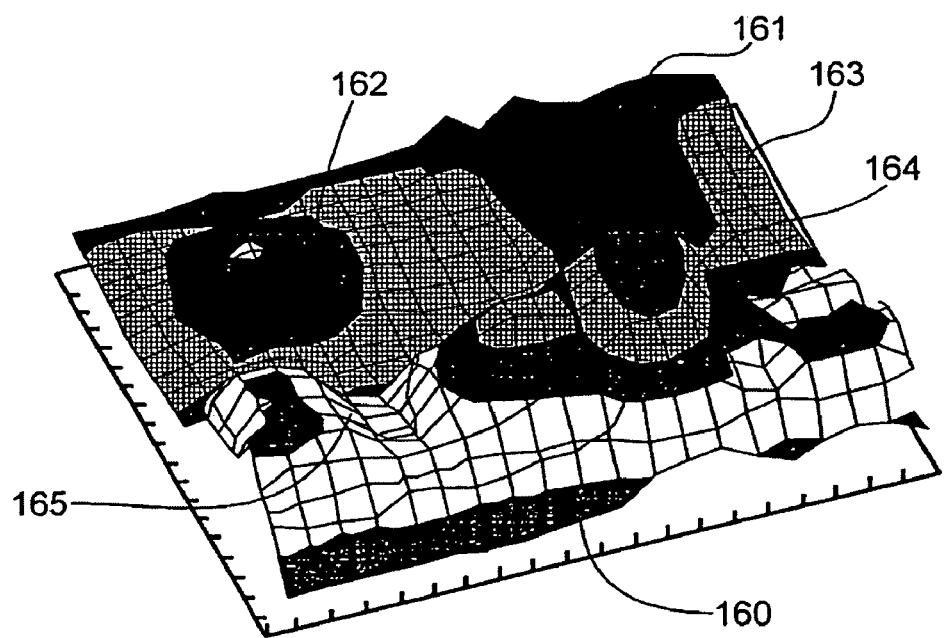
FIG. 17 is a perspective view of a semiconductor LSI showing an example of the film thickness distribution of a transparent film in a semiconductor LSI.

In the examples illustrated in FIGS. 8 and 9, the state of film thickness in the whole wafer can be controlled to a high degree of precision by setting the approximate central regions 85,87 of the chips as the measurement positions during CMP processing. In other words, higher-precision film thickness control for the whole surface of the wafer can be achieved by identifying a wiring pattern section 412 which can readily be processed to a relatively level state, as illustrated in FIG. 5, for measuring the film thickness in each chip of the wafer surface. According to the present invention, the film thickness distribution within the wafer surface can be measured by specifying either relatively even wiring sections or peripheral circuit pattern sections, rather than the border regions between peripheral circuit pattern sections and wiring pattern sections as illustrated in FIG. 17, or the outer circuit sections, which both display large variation in film thickness.

Returning now to FIG. 6, the spectral waveform shown includes the slurry, and, therefore, is a distorted waveform rather than an ideal sinusoidal waveform. The distortion of the waveform is thought to arise because the reflection intensity from the lower pattern below the transparent film is affected by the fact that the difference in refraction index between the transparent film on the pattern and the slurry is less than that between the transparent film and air. In FIG. 6, curve 600 indicates the central trend of the waveform distortion.

Figure 10:
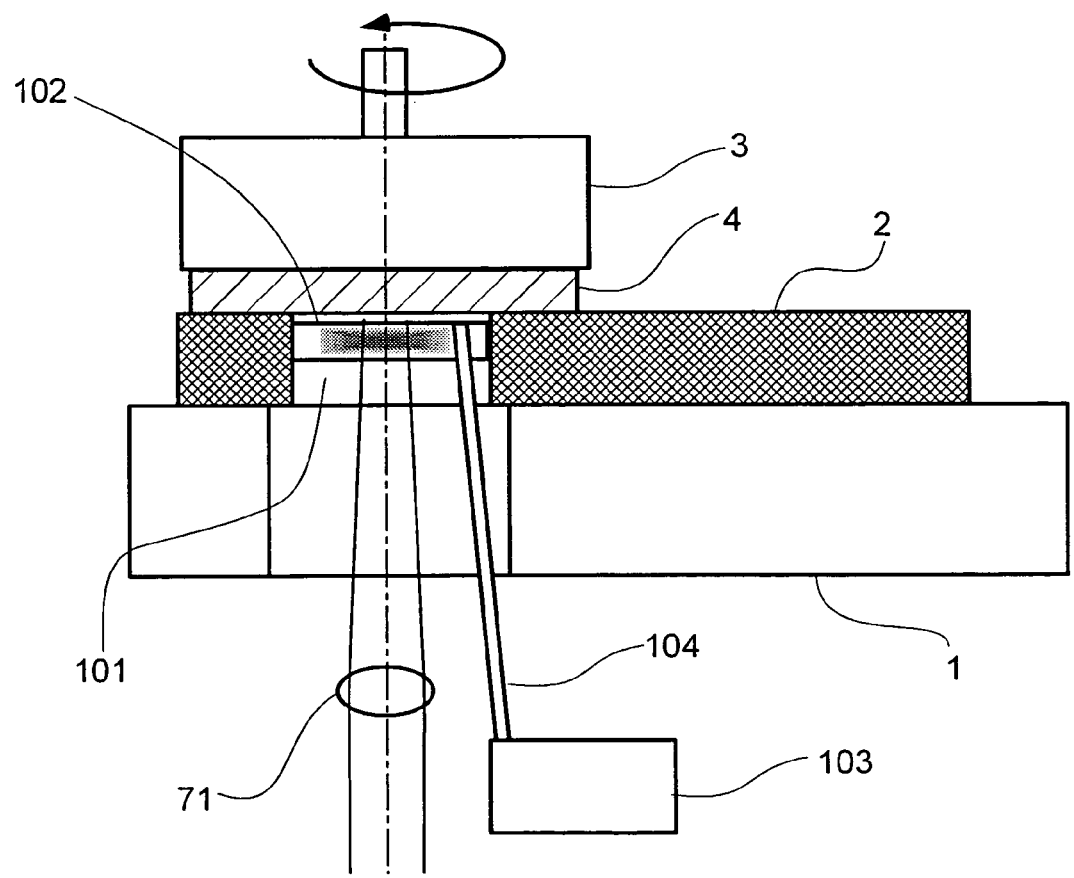
FIG. 10 is a front view showing one example of the structure of a detection window according to the present invention.
Figure 11:
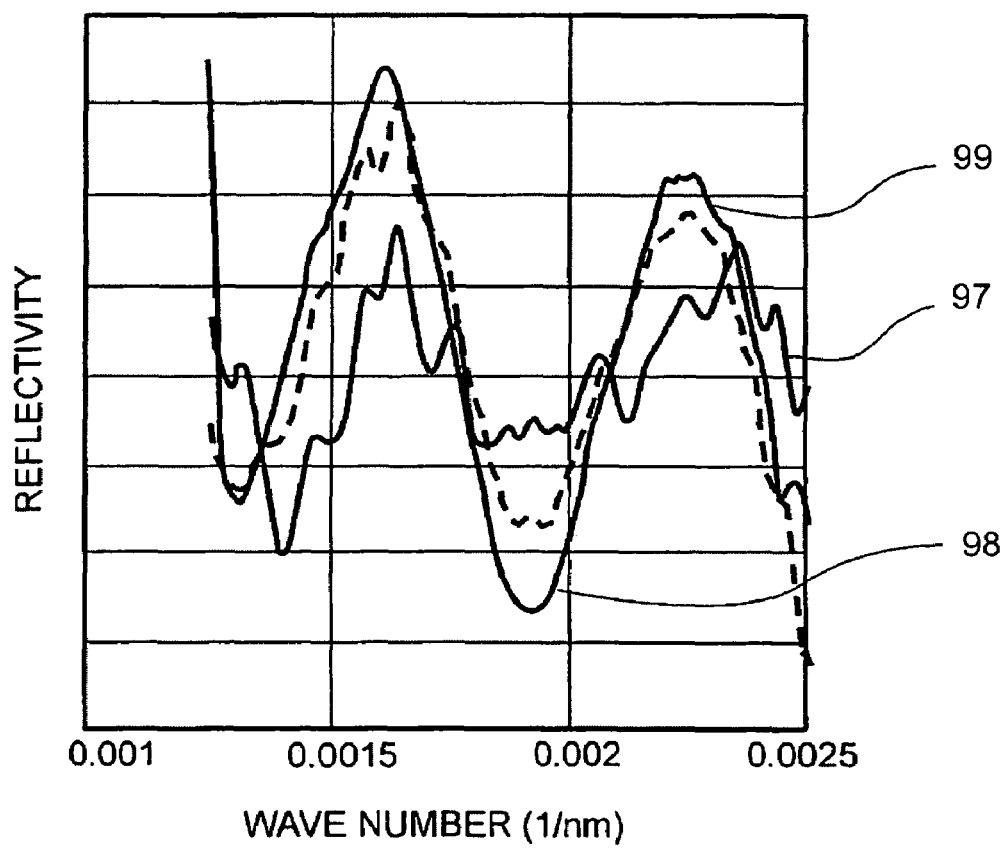
FIG. 11 is a graph showing spectral reflection characteristics for calculating film thickness according to the present invention.

FIG. 11 shows a corrected waveform extracted from the respective waveform envelopes by adding and multiplying the central component, which forms a waveform distortion coefficient, with respect to the spectral waveform in FIG. 6, to eliminate the distortion trend of the spectral waveform. In FIG. 11, spectral waveform 97 corresponds to spectral waveform 61 in FIG. 6; spectral waveform 98 corresponds to spectral waveform 62 in FIG. 6; and spectral waveform 99 corresponds to spectral waveform 63 in FIG. 6. To remove the waveform distortion trend, a method such as that disclosed in Japanese Patent Laid-open No. 2000-310512 may be used, thereby enabling the film thickness to be calculated with high precision by calculating the film thickness from corrected spectral waveforms. FIG. 10 is an explanatory diagram for measuring the spectral waveform of the wafer surface at a high S/N ratio.

In FIG. 10, a window glass 101 has optical characteristics similar to the refraction index of the slurry. For example, a window made of lithium fluoride ($LiF_2$) or magnesium fluoride ($MgF_2$) having a refraction index of approximately 1.4 was used for window glass 81 in the embodiment of FIG. 2. Since the window glass 101 and the slurry 102 have roughly the same refraction index, the reflection component at the border between these respective elements is reduced, and the intensity of reflected light received by the beam splitter increases, thereby improving the S/N ratio of the reflected light after splitting. Moreover, by supplying pure water locally to the slurry 102 in the vicinity of the window glass 101, from a pure water tank 103 via a pipe 104, the slurry 102 is diluted locally, and the slurry solution containing a white suspension, such as ground material or the like, becomes more optically transparent. By detecting the reflected light from the wafer surface via this optically transparent water solution, the reflectivity of the spectral waveform shown in FIG. 6 is increased, and furthermore, waveform distortion due to scattering by ground particles in the slurry, and the like, is reduced, resulting in a spectral waveform more proximate to a sinusoidal wave, thus improving the accuracy of film thickness calculation. The liquid supplied is not limited to pure water, provided that it is a liquid which makes the slurry become optically transparent.

Figure 12:
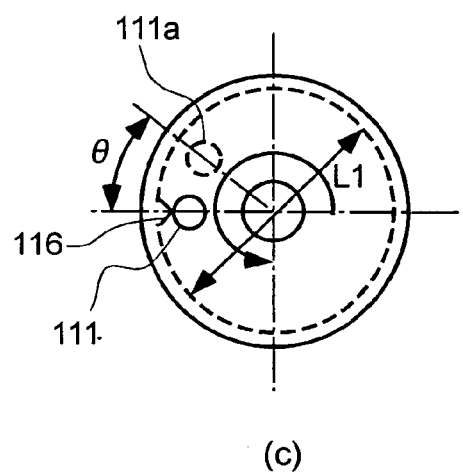
FIG. 12(a) is a front view of a CMP processing device provided with a film thickness measuring means according to the present invention.
FIG. 12(b) is a front view of a CMP processing device according to the present invention.
FIG. 12(c) is a plan view of a holder for a CMP processing device.
Figure 12:
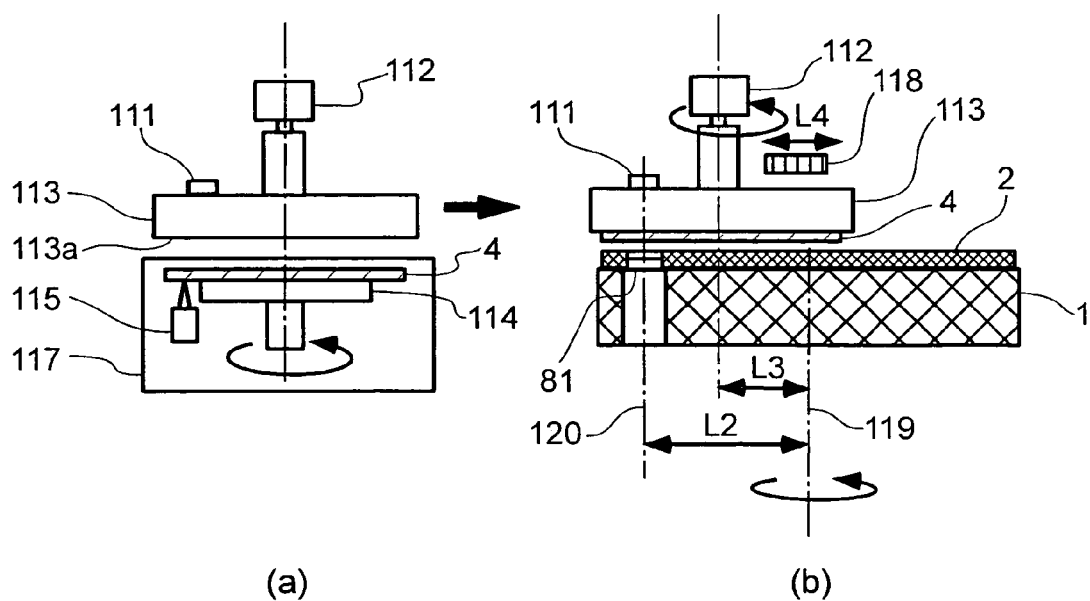
Figure 13:
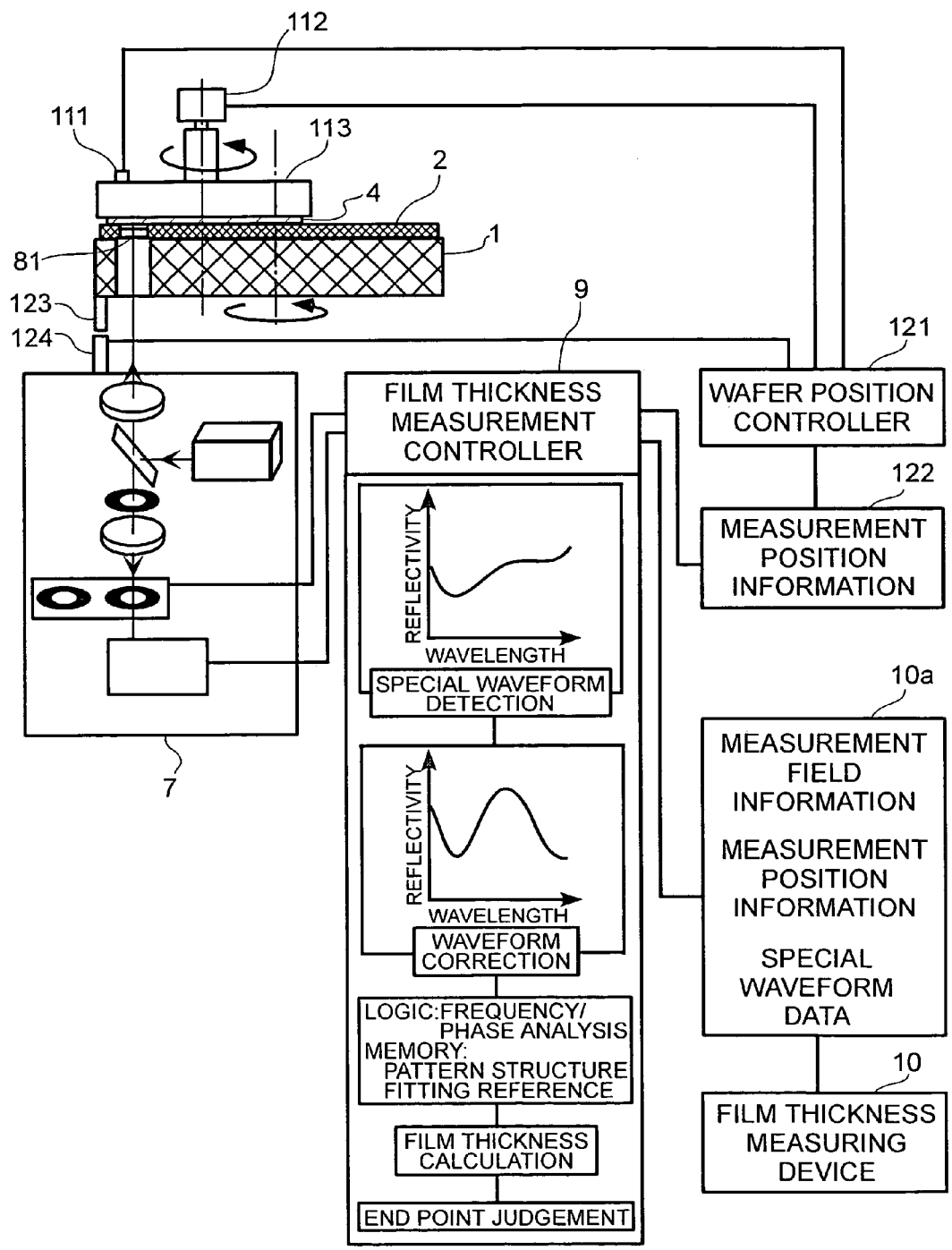
FIG. 13 is a front view showing the general composition of a CMP processing device according to the present invention.

FIGS. 12 and 13 are diagrams for describing a method for controlling the film thickness distribution in a wafer surface by measuring the film thickness distribution for the whole wafer surface during a CMP processing stage.

For FIGS. 12 and 13, descriptions of the configuration and processes which are the same as those described in FIG. 2 are omitted. In these figures, a position sensor 111 and angle of rotation detector 112 are further provided on holder 113, and a wafer position controller 121 is provided for calculating measurement positions by detecting the respective positional and angular information derived therefrom. Furthermore, a sensor 124 is also provided in the vicinity of optical axis 120 of measurement optics system 7, to detect the position of measurement window 81 in the polishing base.

FIG. 12(*a*) illustrates a method for aligning the position of wafer 4 and holder 113. A pre-alignment section 117 consisting of a wafer holder 114 capable of holding and rotating wafer 4, and a notch sensor 115 for detecting a notch in the wafer, is disposed beneath holder 113. In the aforementioned configuration, wafer holder 114 of pre-alignment section 117 is rotated, a notch 116 in the wafer is detected by notch sensor 115, and wafer holder 113 is halted. Next, position sensor 111 on holder 113 is positioned directly above a notch, for example, such that it maintains a relative position with notch 116, and wafer 4 is mounted onto the holding face 113*a* of holder 113. Wafer 4, now held on holding face 113*a* of the holder is then moved over polishing base 1 of the CMP device, and polishing and leveling of the wafer is started. FIG. 12(*b*) shows a general front view of a CMP processing device, and FIG. 12(*c*) shows a partial plan view thereof.

In FIGS. 12(*b*) and (*c*), the outer size L1 of wafer 4, the interval L2 between the center of polishing base 119 and optical axis 120 of measurement optics system 7, and the interval L3 between the center of polishing base 119 and holder 113 are fixed values. Since holder 113 performs a sliding movement, the amount of slide L4 from a central reference point is detected by a slide sensor 118. In this state, the angular position of rotation detector 112 of holder 113 is reset and CMP processing commences. When sensor 124 (shown in FIG. 13) detects a measurement start indicator 123 (shown in FIG. 13) and a measurement start signal is detected by wafer position controller 121 (also shown in FIG. 13), distances L2–L4 on optical axis 120 from the center of wafer 4 at measurement start position 111*a* are set (L2–L4 having been determined by calculating the relative position of optical axis 120 from the wafer center, according to measurement start indicator 123 which has a relative positional relationship with notch 116 at which the wafer diameter L1 is detected). The rotational angle $\theta$ of wafer 4 is also set; and for each revolution of polishing base 1, the measurement positions on the wafer are specified for the film thickness on the basis of the spectral waveforms measured by measurement optics system 7.

Therefore, it is possible to judge whether a chip in the center or the periphery of the wafer surface illustrated in FIG. 9 is being measured. For example, in the case of CMP processing a wafer of $\phi$ 200 mm having $SiO_2$ relative insulation films, the polishing base will process approximately several nm in one revolution (at approximately 100 rpm), and it will process approximately 200 nm in one minute. Since the accuracy of film thickness measurement according to the present invention enables film thickness variations of the order of several tens of nm to be detected, it is also possible for measurement positions to be identified for each revolution of the polishing base 1, and the remaining film thickness calculated and displayed accordingly.

Figure 14:
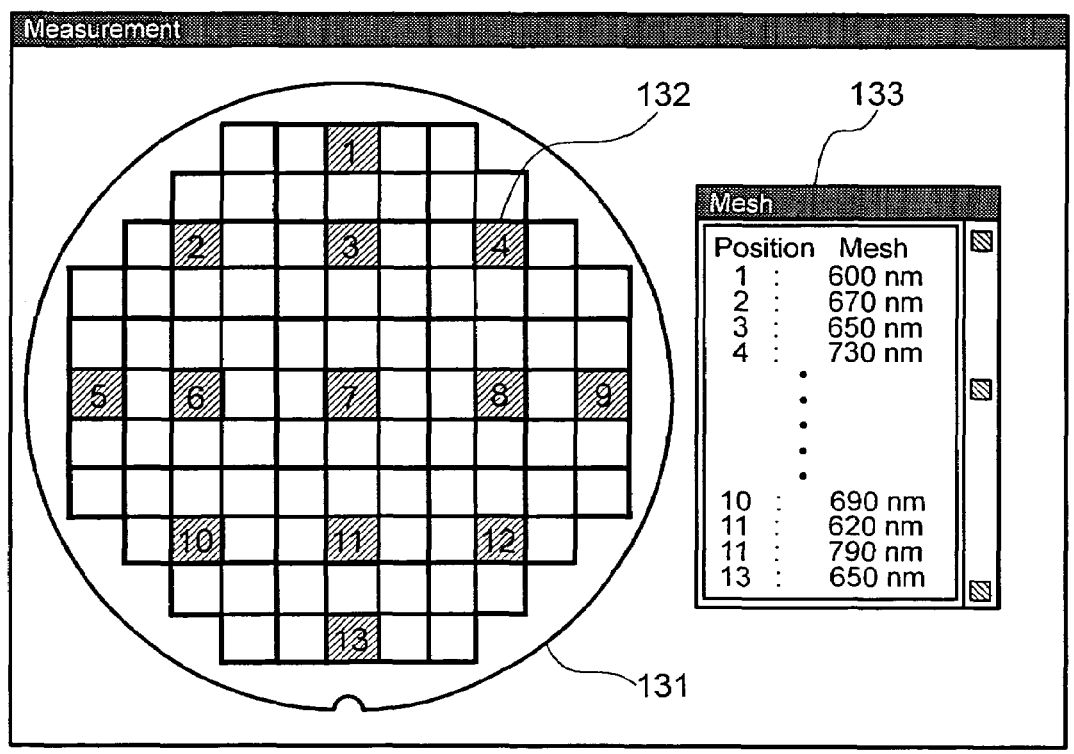
FIG. 14 is a front view of a display screen showing an example of a screen displaying measurement results according to the present invention.
Figure 15:
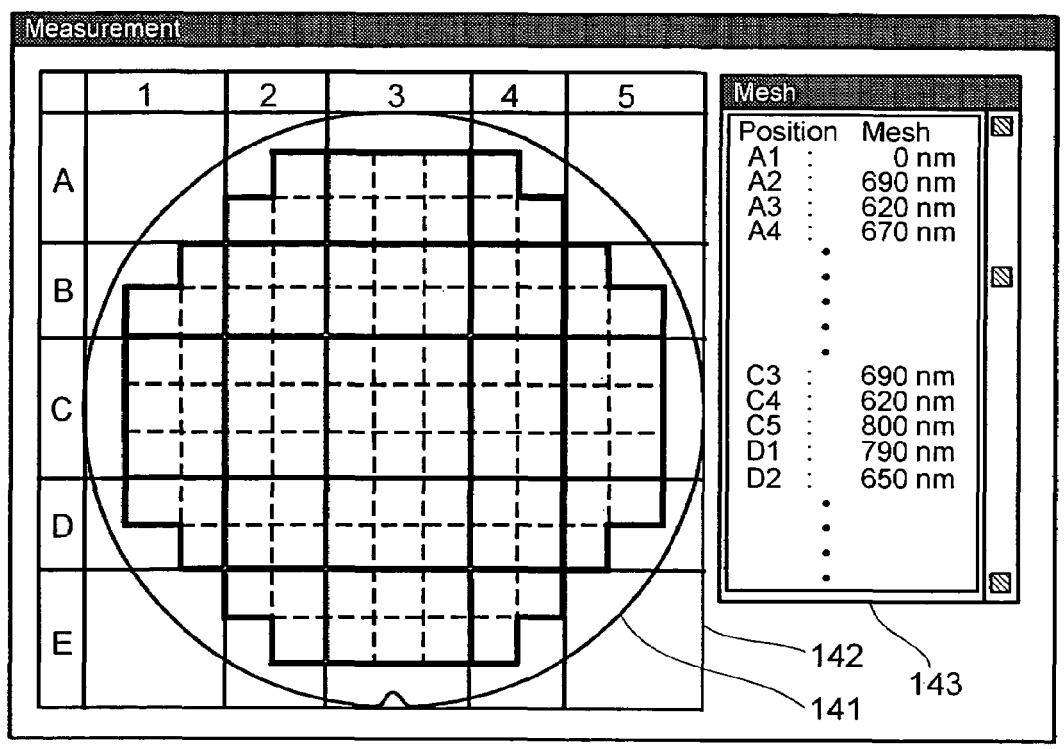
FIG. 15 is a front view of a display screen showing another example of a screen displaying measurement results according to the present invention.

FIGS. 14 and 15 show a state where measurements of the remaining film thickness are displayed. FIG. 14 shows the remaining film thickness for each chip and FIG. 15 shows the remaining film thickness for each region covering a plurality of chips. These results are output in real-time during CMP processing, and the process is terminated when a prescribed remaining film thickness is achieved. The measurement results shown in FIGS. 14 and 15 can be managed as a history for the processed wafer. By appending these measurement results to the wafer and incorporating them into the processing conditions for subsequent processing, and the like, a benefit is attained in that throughput and product quality are improved in the manufacturing process.

Figure 16:
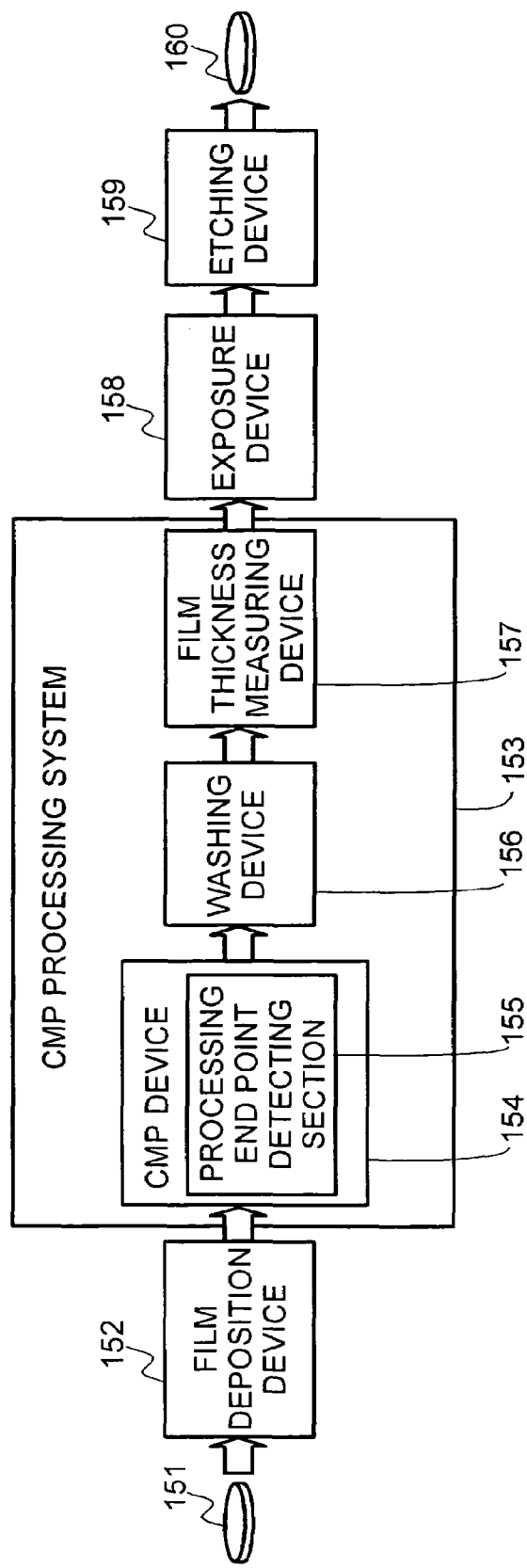
FIG. 16 is a process diagram showing an example of processing stages for manufacturing a semiconductor device using a CMP processing system according to the present invention.

FIG. 16 is a diagram illustrating a manufacturing method for a semiconductor device according to the present invention. In this method, a thin film is formed on the surface of a wafer 151 by sputtering, or the like, using a film deposition device 152, whereupon the wafer is conveyed to a CMP processing stage 153. In CMP processing stage 153, the film is processed to an even thickness by means of a CMP device 154, while the film thickness on the surface of wafer 151 is controlled by means of a process end point detecting section 155 implementing a method described in the aforementioned embodiments. The processed wafer is then washed by a washing device 156, and if necessary, the film thickness at prescribed locations on wafer 151 is measured by means of a film thickness measuring device 157. This measurement of the film thickness by measuring device 157 need not necessarily be performed for the whole wafer, but may, instead, be performed for a selected wafer or number of wafers, according to requirements. The wafer having undergone CMP processing stage 153 is then formed with wiring patterns, and the like, by passing through an exposure device stage 158, and an etching stage 159, whereupon it is conveyed to subsequent processes.

In the present invention, since the measurement of the film thickness in the CMP processing stage can be carried out during CMP processing, and, moreover, since the film thickness can be measured at specified positions on the wafer, it is possible to improve the evenness of the wafer surface after processing—significantly, compared to conventional techniques—by supplying CMP device 154 with these film thickness measurement results as feedback into the CMP processing conditions(e.g., slurry conditions: material, density, supply rate; pad conditions: material, shape, dressing, replacement schedule, and the like; polishing revolution rate; wafer holding pressure; and the like). In this way, a wafer having a surface of significantly improved evenness after CMP processing is realized, and through subsequent exposure and etching processes, it is possible to form fine patterns having very high reliability.

The film thickness measurement results for thickness distribution across the wafer surface can also be appended to wafer 151 after it has been CMP processed, while monitoring film thickness as in the present invention. By using these appended measurement results, the etching conditions in the etching process 159 (etching time, applied voltage, gas supply volume, etc.) can be controlled to optimum conditions, and a semiconductor wafer 160 of very high quality can be manufactured.

According to the present invention, it is possible to perform high-precision film thickness measurement of a transparent film on a semiconductor device during a CMP process. Accordingly, highly accurate control of the polishing process can be achieved on the basis of the measured film thickness data. Furthermore, because the film thickness distribution in the surface of the silicon wafer (substrate) of the semiconductor device being polished can be controlled to a high degree of accuracy, it is possible to improve the leveling process in the CMP processing stage based on this film thickness distribution, and also to optimize the film deposition conditions in the film deposition stage, and the processing conditions in the etching stage, thereby enabling the manufacture of a high-precision system device. In addition, the end point for a CMP process in the aforementioned method and production line for manufacturing semiconductor devices on a silicon wafer, can be detected with a high degree of accuracy; therefore the throughput of the process can be improved.

The invention may be embodied in other specific forms without departing from the spirit or essential characteristics thereof. The present embodiment is therefore to be considered in all respects as illustrative and not restrictive. The scope of the invention is indicated by the appended claims rather than by the foregoing description and all changes which come within the meaning and range of equivalency of the claims are therefore intended to be embraced therein.

What is claimed is:

1. A method for manufacturing thin film devices comprising:
   during a polishing process, irradiating white light onto a thin film device having an optically transparent film formed thereon;
   detecting light reflected from said thin film device due to the irradiation of said white light when said thin film device is at a predetermined position, a position of said thin film device being determined based on information from a position sensor and a rotation detector;
   calculating a spectral waveform of said detected light;
   correcting distortions in the spectral waveform; and
   determining a thickness of said optically transparent film at said predetermined position using information from the spectral waveform of the light thus detected.

2. The method for manufacturing thin film devices according to claim 1, wherein said predetermined position is determined on the basis of previously measured information for the film thickness distribution of thin film devices created by the same process as said thin device.

3. A method for manufacturing thin film devices comprising:
   determining a set of measurement positions on a thin film device on the basis of spectral waveform information;
   (i) during a polishing process, irradiating white light onto an optically transparent film formed on said thin film device when said thin film device is at one of said measurement positions, a position of said thin film device being determined based on information from a position sensor and a rotation detector;
   (ii) detecting light reflected from said thin film device due to the irradiation of said white light;
   (iii) calculating a spectral waveform of said detected light;
   (iv) correcting distortions in the spectral waveform of said reflected light;
   (V) determining a thickness of said optically transparent film at said one of said measurement positions using information from the corrected spectral waveform of the reflected light; and
   monitoring said polishing process by performing steps (i) through (v) for one or more of said measurement positions.

4. The method for manufacturing thin film devices according to claim 3, wherein the measurement positions are determined based on a predetermined characteristic quantity of said spectral waveform information.

5. The method for manufacturing thin film devices according to claim 3, wherein said predetermined position for measuring film thickness is determined using the reflectivity of said thin film device with respect to said white light.

6. The method for manufacturing thin film devices according to claim 3, wherein said measurement positions for measuring film thickness are determined using a frequency spectrum of said spectral waveform of said reflected light.

7. A method for manufacturing thin film devices comprising:

setting measurement positions for determining a thickness of an optically transparent film formed on the surface of a thin film device;
(i) during a polishing process, irradiating white light onto said optically transparent film when said thin film device is at one of said measurement positions, a position of said thin film device being determined based on information from a position sensor and a rotation detector;
(ii) detecting light reflected from said thin film device due to the irradiation of said white light;
(iii) calculating a spectral waveform of said detected light;
(iv) correcting distortions in the spectral waveform;
(v) determining a thickness of said optically transparent film at said one of said measurement positions on the basis of the corrected spectral waveform; and
monitoring said polishing process by performing steps (i) through (v) for one or more of said measurement positions.

8. The method for manufacturing thin film devices according to claim 7, wherein a plurality of measurement positions for determining said film thickness are set, the film thickness at each of the plurality of measurement positions thus set is determined, information relating to the film thickness distribution on said thin film device is obtained, and said polishing process is monitored using the information relating to the film thickness distribution thus obtained.

9. A method for manufacturing thin film devices comprising:

(i) during a polishing process, irradiating white light onto an optically transparent film formed on a thin film device when said thin film device is at a predetermined position, a position of said thin film device being determined based on information from a position sensor and a rotation detector;
(ii) detecting light reflected from said thin film device due to the irradiation of said white light;
(iii) calculating a spectral waveform of said detected light;
(iv) correcting distortions in the spectral waveform;
(v) determining a thickness of said optically transparent film at said predetermined position using information relating to said corrected spectral waveform of the reflected light; and
monitoring said polishing process by performing steps (i) through (v) for said predetermined measurement position.

10. The method for manufacturing thin film devices according to claim 9, wherein the information relating to said corrected spectral waveform is the reflection intensity of said corrected spectral waveform.

11. The method for manufacturing thin film devices according to claim 9, wherein the information relating to said corrected spectral waveform is the frequency spectrum intensity of said corrected spectral waveform.

* * * * *